(12) United States Patent
Jaffee et al.

(10) Patent No.: US 10,048,266 B2
(45) Date of Patent: Aug. 14, 2018

(54) DIAGNOSTIC BIOMARKERS AND THERAPEUTIC TARGETS FOR PANCREATIC CANCER

(71) Applicant: The Johns Hopkins University, Baltimore, MD (US)

(72) Inventors: Elizabeth A. Jaffee, Lutherville, MD (US); Darshil T. Jhaveri, Towson, MD (US); Robert Anders, Parkville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/809,555

(22) Filed: Nov. 10, 2017

(65) Prior Publication Data
US 2018/0120322 A1    May 3, 2018

Related U.S. Application Data

(60) Division of application No. 15/148,674, filed on May 6, 2016, now abandoned, which is a continuation of application No. 14/649,248, filed as application No. PCT/US2013/072592 on Dec. 2, 2013, now abandoned.

(60) Provisional application No. 61/732,402, filed on Dec. 3, 2012.

(51) Int. Cl.
*G01N 33/574* (2006.01)

(52) U.S. Cl.
CPC .......... *G01N 33/57438* (2013.01); *G01N 2333/4703* (2013.01); *G01N 2333/705* (2013.01); *G01N 2333/79* (2013.01); *G01N 2333/916* (2013.01)

(58) Field of Classification Search
None
See application file for complete search history.

(56) References Cited

U.S. PATENT DOCUMENTS

| 4,208,479 | A | 6/1980 | Zuk et al. |
| 2002/0111308 | A1 | 8/2002 | Pyle et al. |
| 2006/0039908 | A1 | 2/2006 | Mather et al. |
| 2009/0023149 | A1 | 1/2009 | Knudsen |
| 2011/0293608 | A1 | 12/2011 | Jaffee et al. |
| 2013/0177579 | A1 | 7/2013 | Lin et al. |

OTHER PUBLICATIONS

Gaudernack et al. (Best Practice & Research Clinical Gastroenterology 2006 vol. 20, p. 299-314) (Year: 2006).*
Gjertsen et al. (Int. J. Cancer 1996 vol. 65, p. 450-453) (Year: 1996).*
Gjertsen (II) et al. (Int. J. Cancer 2001 vol. 92, p. 441-450) (Year: 2001).*
Berberat et al., Journal of Histochemistry and Cytochemistry., 2001. vol. 49, pp. 539-549.
Ryschich, et al., "Transferrin receptor is a marker of malignant phenotype in human pancreatic cancer and in neuroendocrine carcinoma of the pancreas", European Journal of Cancer, vol. 40, No. 9 pp. 1418-1422 (2004).
Roe et al., "Malignant pleural mesothelioma: genome-wide expression patterns reflecting general resistance mechanisms and a proposal of novel targets", Lung Cancer, vol. 67, No. 1 pp. 57-68 (2010).
Pan et al., "Protein alterations associated with pancreatic cancer and chronic pancreatitis found in human plasma using global quantitative proteomics profiling", Journal of Proteome Research, vol. 10, No. 5, pp. 2359-2376 (2011).
Jhaveri et al.,"Abstract 2485: A novel quantitative proteomics approach to identify proteins that elicit antibody responses in vaccinated pancreatic cancer patients", Cancer Research, vol. 73, Issue 8, Supplement 1 (Apr. 15, 2013).
International Search Report and Written Opinion dated Mar. 14, 2014, for PCT/US2013/072592.

* cited by examiner

*Primary Examiner* — Changhwa J Cheu
(74) *Attorney, Agent, or Firm* — Mintz Levin Cohn Ferris Glovsky and Popeo, P.C.; Peter F. Corless

(57) ABSTRACT

We identified >40 proteins that elicited at least a 2-fold increase in antibody response post-pancreatic-cancer vaccination, from each of three patients' sera. The antibody responses detected against these proteins in patients with >3 years disease-free survival indicates the anti-tumor potential of targeting these proteins. We found that tissue expression of proteins PSMC5, TFRC and PPP1R12A increases during tumor development from normal to pre-malignant to pancreatic tumor. In addition, these proteins were shown to be pancreatic cancer-associated antigens that are recognized by post-vaccination antibodies in the sera of patients that received the vaccine and have demonstrated a favorable disease free survival.

3 Claims, 17 Drawing Sheets

Fig. 4

| | Pre-vaccination | Post-vaccination | Fold Change (Post-vaccination/Pre-vaccination) |
|---|---|---|---|
| Galectin-3 | | | 15.3 |
| E3 ubiquitin-protein ligase UBR5 | | | 4.0 |
| Mesencephalic astrocyte-derived neurotrophic factor | | | 3.9 |
| Calpain-1 | | | 0.4 |
| Epidermal growth factor receptor kinase substrate 8-like protein 2 | | | 0.1 |

Fig. 6A.   PSMC5
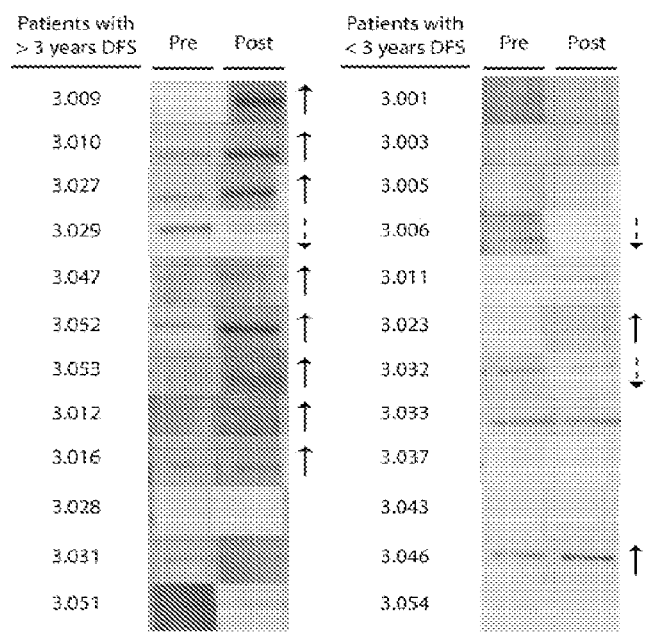
Fig. 6B.   TFRC
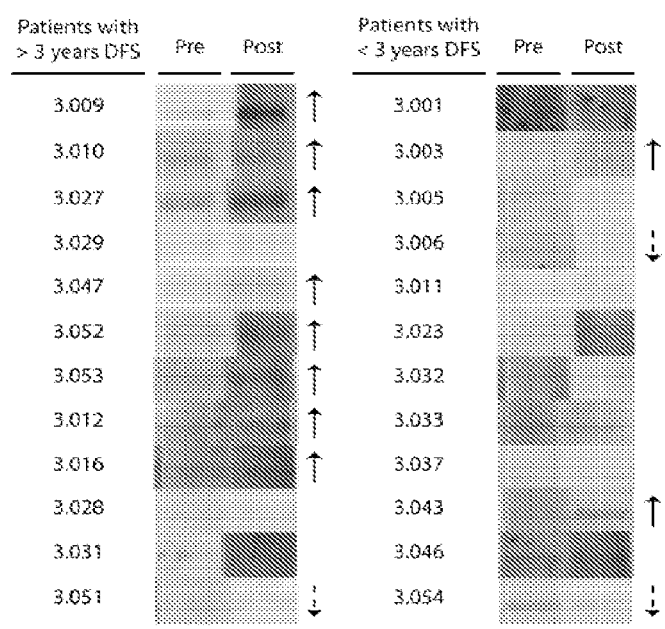

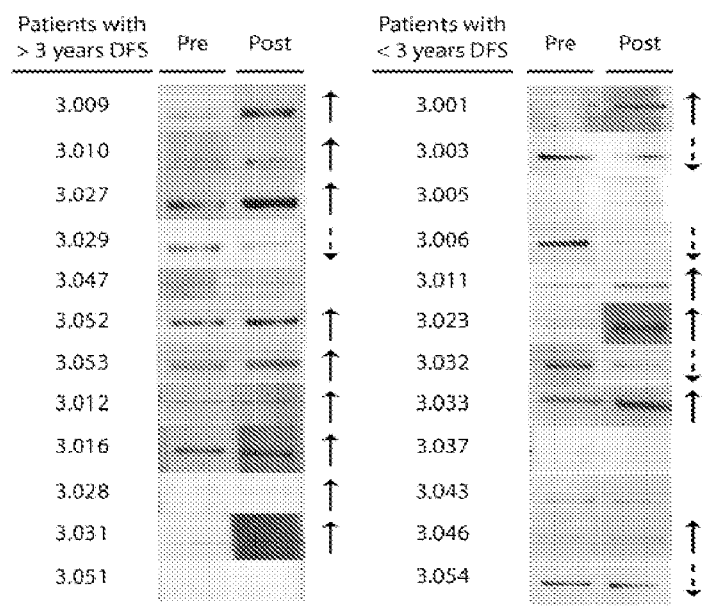

Fig. 10A
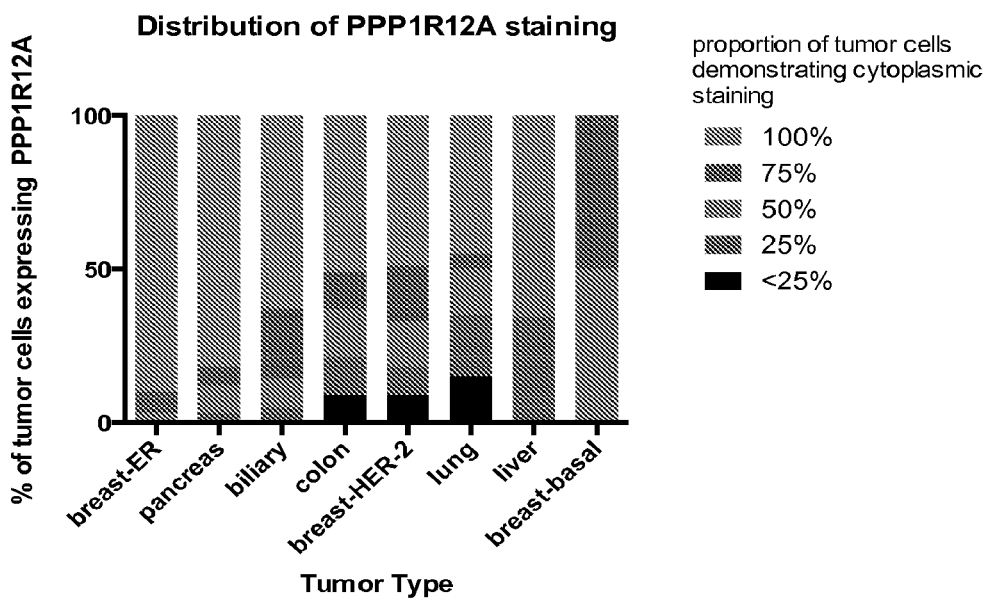
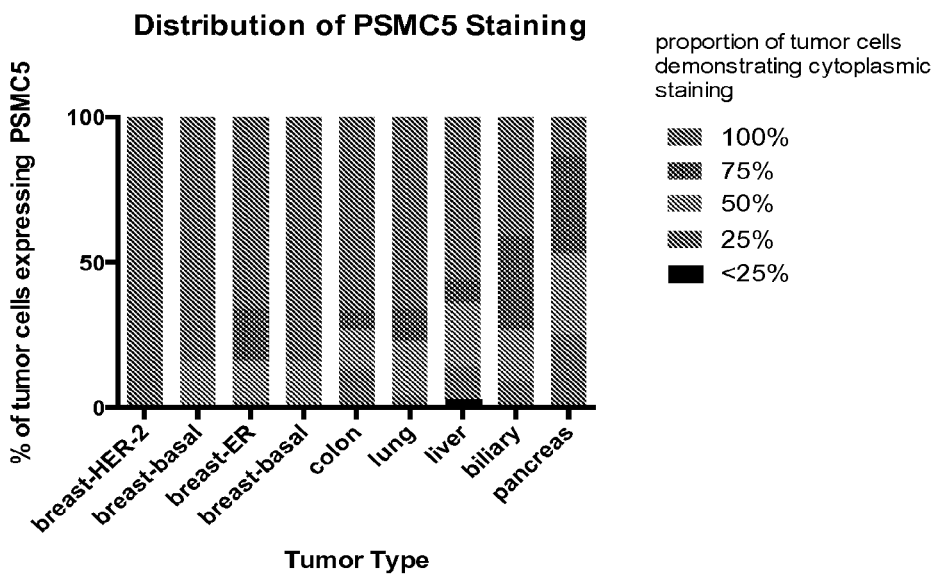
Fig. 10B

DIAGNOSTIC BIOMARKERS AND THERAPEUTIC TARGETS FOR PANCREATIC CANCER

CROSS REFERENCE TO RELATED APPLICATIONS

This application is a divisional of U.S. application Ser. No. 15/148,674, filed May 6, 2016 which is a continuation of U.S. application Ser. No. 14/649,248, filed on Jun. 3, 2015, which is a national stage entry of International Application No.: PCT/US2013/072592, filed on Dec. 2, 2013, which claims priority to U.S. Provisional Patent Application No. 61/732,402, filed on Dec. 3, 2012, each of which is incorporated herein by reference in its entirety.

FEDERALLY SPONSORED RESEARCH OR DEVELOPMENT

This invention was made with government support under Grant No. P50CA62924 awarded by the National Institutes of Health/National Cancer Institute. The government has certain rights in the invention.

TECHNICAL FIELD OF THE INVENTION

This invention is related to the area of cancer diagnostics, prognostics, and therapeutics. Moreover, it relates to the area of immunotherapeutics.

BACKGROUND OF THE INVENTION

Pancreatic ductal adenocarcinoma is the fourth leading cause of cancer-related death in the U.S. (1). It is notably the most aggressive and debilitating malignant disease with a median survival of less than 6 months. Only 1% to 4% of patients have an overall survival of more than 5 years (1). Inadequate early diagnosis, resistance to current therapies, and ineffective treatment account for these low survival statistics. Alternative treatment approaches are desparately needed for this disease; the compelling need for superior treatment options has propelled the development of new, better-targeted therapies. We have developed an allogeneic, granulocyte-macrophage colony-stimulating factor (GM-CSF)-secreting pancreatic cancer vaccine, which has recently completed phase II clinical trial (2). This promising vaccine is used in combination with chemoradiation. The observation of favorable clinical and immunological responses in patients has testified to the success of the vaccine (2-4). It was shown that the induction of mesothelin-specific T cell responses only in patients with a DFS>3 years, which suggests the vaccine induces immunologically relevant T cell responses (2). Functional genomic approaches were utilized to identify antigens recognized by T cells (5). However, finding T cell antigens is limited by the need for large amounts of patient lymphocytes and the lack of reagents for each patient-specific HLA (6).

In contrast to T cells, antibodies hold potential as a high throughput way of identifying antigens. Antibodies can also mount an effective response against cancer cells through opsonizing, antigen presentation to T-cells, and mediating cell toxicity via natural killer cells or the complement system (7). Thus, the application of seroproteomic approaches has recently gained ground in the identification of new cancer biomarkers. These cancer biomarkers are beneficial for both early detection and the determination of new targets for the development of biologically relevant therapies (7-12). The most well-known proteomic approaches utilize sera from untreated cancer patients or individuals with known genetic susceptibilities for cancer, to screen for cancer-associated proteins that elicit an antibody response. These approaches identify oncoproteins that elicit an antibody response due to differences in expression levels or post-translational modifications (11). GM-CSF secreting cancer vaccines can also instigate a broad range of antibody responses, as seen in early clinical studies (13). Through the study of the immunological responses in vaccinated patients, we can discover the mechanisms behind favorable vaccine-induced clinical responses. Identifying cancer associated proteins will enhance our efforts of identifying biologically relevant proteins. These proteins have high potential as future targets for effective pancreatic cancer treatment. This translational approach will advance the development of new drugs, vaccines and antibody-based therapies that will halt the progression and metastasis of the disease. This approach can also help characterize new proteins that will serve as surrogate biomarkers, prediction tools of the vaccine's success, and biomarkers for early diagnosis of pancreatic cancer.

Common proteomic approaches to identify immunogenic proteins are: Serological Screening of cDNA Expression Library (SEREX), 2-dimensional electrophoresis (2-DE) followed by mass-spectrometry analysis and protein arrays (7). Proteins found using SEREX and 2-DE approaches are now shown to also elicit T cell responses (6, 13, 14). This provides evidence that antibodies can aid in the identification of T cell antigens, which further testifies to the advantages in studying antibodies. SEREX, however, utilizes proteins expressed in *Escherichia coli*, which does not account for human post-translational modifications (12). Contrastingly, the approach utilizing 2-DE analysis can use human proteins as the proteome. However, this process has an inherent bias towards identifying proteins that are abundantly expressed (11). 2D-PAGE has a lower threshold out of the throughput methods and does not effectively identify proteins that are very acidic, very basic, small in size (<15 kDa), or hydrophobic (15). Therefore, this process is inadequate for detecting membrane-associated proteins, the most relevant category of proteins as potential biomarkers. Membrane proteins constitute about 30% of all cellular proteins and are functionally key regulators (16). In addition, in 2D-PAGE, each band cut holds several similar molecular weight proteins. This process is inefficient in separating single proteins, which obscures which protein instigates the antibody response. Furthermore, low abundant antigens are generally overshadowed by high abundant proteins with the same molecular weight in this process. Both SEREX and SERPA identify linear epitopes, are relatively low throughput and semi-quantitative (11). Protein arrays come in many forms. Some protein arrays use tumor cell lysate fractions, which identify proteins in their native conformation (11). However, these arrays do not identify which specific protein in the fraction instigates the immune response and there also issues with fractionation. The protein arrays with printed recombinant proteins do not contain human post-translational modifications because the proteins are expressed in *E. coli* or yeast (12). In addition, if a known protein panel is printed, tumor antigen discovery can be prevented because the proteome is biased. The protein arrays utilizing printed monoclonal antibodies are potentially limited by reagent availability thereby preventing an unbiased proteome being used because a high affinity and highly specific monoclonal antibody is needed for each protein to be probed.

There is a continuing need in the art to provide better methods of early diagnosis, monitoring, prognosing, and treating pancreatic cancer.

SUMMARY OF THE INVENTION

According to one embodiment of the invention a method detects pancreatic cancer in a body sample from a human. A body sample is contacted with at least one antibody that specifically binds to a protein selected from the group consisting of: Transferrin receptor (TFRC), regulatory subunit 12A of protein phosphatase 1 (PPP1R12A), and regulatory subunit 8 of the 26S proteasome (PSMC5). The amount of antigen bound to the antibody is detected or cellular localization of the antigen is detected. An increased amount of antigen bound to the antibody relative to an amount bound to a control sample or an altered cellular localization indicates the presence of a pancreatic cancer.

According to another embodiment a method monitors progression of pancreatic cancer in a body sample from a human. A body sample is contacted with at least one antibody that specifically binds to a protein selected from the group consisting of: Transferrin receptor (TFRC), regulatory subunit 12A of protein phosphatase 1 (PPP1R12A), and regulatory subunit 8 of the 26S proteasome (PSMC5). The amount of antigen bound to the antibody is detected. An increased amount of antigen bound to the antibody relative to an amount bound to a sample taken at a prior time indicates progression of the pancreatic cancer. A decreased amount of antigen bound to the antibody relative to amount bound to a sample taken at a prior time indicates responsiveness to an anti-cancer treatment.

According to another embodiment a method predicts response to a pancreatic cancer vaccine in a human. A body sample of the human is contacted with at least one antibody that specifically binds to a protein selected from the group consisting of: Transferrin receptor (TFRC), regulatory subunit 12A of protein phosphatase 1 (PPP1R12A), and regulatory subunit 8 of the 26S proteasome (PSMC5). The amount of antigen bound to the antibody is detected. A decreased amount of antigen bound to the antibody relative to an amount bound to a control sample prior to vaccination predicts long term disease-free survival.

According to another embodiment a kit is provided for detecting or monitoring pancreatic cancer disease or therapy. The kit contains at least one antibody that specifically binds to an antigen selected from the group consisting of: Transferrin receptor (TFRC), regulatory subunit 12A of protein phosphatase 1 (PPP1R12A), and regulatory subunit 8 of the 26S proteasome (PSMC5). The kit further contains a detection means for detecting binding complexes of the antibody and antigens in a test sample.

According to another embodiment a method predicts response to a pancreatic cancer vaccine in a human. A sample of the human comprising antibodies is contacted with at least one protein selected from the group consisting of: Transferrin receptor (TFRC), regulatory subunit 12A of protein phosphatase 1 (PPP1R12A), and regulatory subunit 8 of the 26S proteasome (PSMC5). The amount of antibody bound to the at least one protein is detected. An increased amount of antibody bound to the at least one protein relative to an amount bound to a control sample obtained prior to vaccination predicts long term disease-free survival. According to another embodiment a kit is provided for detecting or monitoring pancreatic cancer disease or therapy. The kit comprises at least one protein selected from the group consisting of: Transferrin receptor (TFRC), regulatory subunit 12A of protein phosphatase 1 (PPP1R12A), and regulatory subunit 8 of the 26S proteasome (PSMC5). The kit further comprises a detection means for detecting binding complexes of the protein with an antibody in a test sample.

According to one embodiment of the invention a method tests a body sample from a human. A body sample is contacted with at least one antibody that specifically binds to a protein selected from the group consisting of: Transferrin receptor (TFRC), regulatory subunit 12A of protein phosphatase 1 (PPP1R12A), and regulatory subunit 8 of the 26S proteasome (PSMC5). The amount of antigen bound to the antibody is detected or cellular localization of the antigen is detected. An increased amount of antigen bound to the antibody relative to an amount bound to a control sample or an altered cellular localization is detected.

According to another embodiment a method tests a body sample of a human with pancreatic cancer. A first body sample is contacted with at least one antibody that specifically binds to a protein selected from the group consisting of: Transferrin receptor (TFRC), regulatory subunit 12A of protein phosphatase 1 (PPP1R12A), and regulatory subunit 8 of the 26S proteasome (PSMC5). The amount of antigen bound to the antibody is detected. The amount detected in the first body sample is compared to the amount detected in a second body sample taken from the human at a second time.

According to another embodiment a method tests a body sample of a human. A first and second body samples of the human are contacted with at least one antibody that specifically binds to a protein selected from the group consisting of: Transferrin receptor (TFRC), regulatory subunit 12A of protein phosphatase 1 (PPP1R12A), and regulatory subunit 8 of the 26S proteasome (PSMC5). The amount of antigen bound to the antibody is detected in each sample. The amount detected in each sample is compared to the other. The first and second body samples of the human are collected at a first and second time, wherein the first time is before and the second time is after the human is vaccinated with a pancreatic cancer vaccine composition.

According to another embodiment a method tests a body sample of a human who has received a pancreatic cancer vaccine. A sample of the human which comprises antibodies is contacted with at least one protein selected from the group consisting of: Transferrin receptor (TFRC), regulatory subunit 12A of protein phosphatase 1 (PPP1R12A), and regulatory subunit 8 of the 26S proteasome (PSMC5). The amount of antibody bound to the at least one protein is detected. The amount of antibody detected in the sample of the human who has received a pancreatic cancer vaccine is compared to the amount detected in a sample of the human before he or she received the vaccine.

These and other embodiments which will be apparent to those of skill in the art upon reading the specification provide the art with methods and kits for better managing pancreatic cancer.

BRIEF DESCRIPTION OF THE DRAWINGS

FIG. 4. Validation of mass-spectrometry derived SILAC data using Western-blots. The fold-change detected by mass spectrometry is shown to the right of each blot.

FIGS. 6A to 6C. Increased antibody response post-vaccination correlates with improved survival. Solid arrow shows an increase post-vaccination whereas a dotted arrow shows a decrease post-vaccination in antibody response. FIG. 6A: PSMC5; FIG. 6B: TFRC; FIG. 6C: PPP1R12A FIG. 7A-7B. PSMC5 staining by immunohistochemistry N: Normal duct cells, C: Cancer cells FIG. 8A-8C. PPP1R12A staining by IHC. N: Normal duct cells, C: Cancer cells, I: Isotype control FIG. 9. TFRC staining by MC. N: Normal duct cells, C: Cancer cells FIG. 10. Tumor microarrays were scored for the percentage of cells that express cytoplasmic PPP1R12A (FIG. 10A) or PSMC5 (FIG. 10B). The distribution of positive staining cells was classified into <25%, 25%, 50%, 75%, or 100% of tumor cells present. The frequency of each percentage is plotted in the above histograms. Tumors with expression patterns significantly different than pancreas are noted with an * indicated P<0.01.

DETAILED DESCRIPTION OF THE INVENTION

Figure 1:
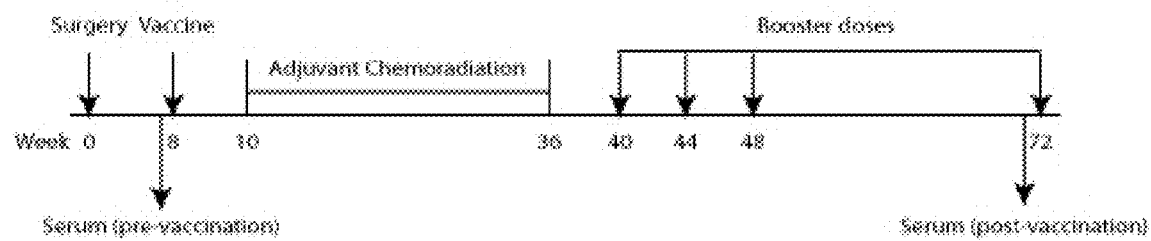
FIG. 1. The vaccination schedule we used.

The inventors have identified three different proteins that are strongly overexpressed in pancreatic cancer whereas they are either weakly or not expressed at all in pancreatic normal duct cells. These proteins are also shown to be targets of a clinically relevant antibody response induced with a vaccination. Thus, we have identified candidate proteins as new biomarkers for screening, and as new targets for therapeutic intervention.

Samples which can be tested include any body sample in which pancreatic cancer proteins are expressed or shed. These include without limitation blood, urine, stool, pancreatic tissue samples, metastatic tissue samples, lymph, lymph nodes.

Any immunological detection technique can be used as is convenient. These include without limitation ELISA, immunoprecipitation, immunonblots, radioimmunoassays, protein arrays, and antibody arrays.

Amounts of antigen can be detected by preparing and comparing to a standard curve, for example. Amounts may also be determined relatively, by comparing to a relevant control sample, such as a sample of the same type obtained from the patient at a different time, or obtained from a tissue known to be non-cancerous, or a sample obtained from one or a population of normal patients.

One, two, or three of the identified markers (Transferrin receptor (TFRC), regulatory subunit 12A of protein phosphatase 1 (PPP1R12A), and regulatory subunit 8 of the 26S proteasome (PSMC5)) may be used as a panel. Additional markers including mesothelin, annexin A2, and galectin 3 may be used. Other clinical parameters may be used and combined to render a diagnosis or prognosis or assessment of current or future response to a therapy. The amount of protein (Transferrin receptor (TFRC), regulatory subunit 12A of protein phosphatase 1 (PPP1R12A), and regulatory subunit 8 of the 26S proteasome (PSMC5)) in a sample can be used as a measure of the disease. Alternatively, the amount of antibody that a patient is producing to these proteins can be determined as a measure of a specific and clinically relevant immune response.

Any type of antibody can be used for measurement of protein in a sample. L Antibodies which can be used to measure proteins may be polyclonal, monoclonal, single chain, chimeric, or hybrid, for example. Antibodies can be conjugated to other functionalities to aid in the detection of the antibodies in an antigen-antibody complex. Secondary antibodies or radiolabels can be used to detect antibodies, for example.

Kits can be made with the antibodies or proteins (Transferrin receptor (TFRC), regulatory subunit 12A of protein phosphatase 1 (PPP1R12A), and regulatory subunit 8 of the 26S proteasome (PSMC5)) useful in carrying out the various described methods. The kits may have one, two, or three of the described antibodies or proteins. Additional antibodies or proteins can also be included for further refinements. Detection means such as enzymes or radiolabels or secondary antibodies may also be included. Buffers and other necessary reagents may be included. Instructions may be included in the kits. The kits' components may be in a divided or undivided container. A main container may contain sub-containers.

For detection of antibodies in patient samples, preferably the reagents used will be purified proteins (e.g., Transferrin receptor (TFRC), regulatory subunit 12A of protein phosphatase 1 (PPP1R12A), and regulatory subunit 8 of the 26S proteasome (PSMC5)), although they need not be. The proteins may be made in recombinant cells or purified from a natural source. The proteins or portions thereof may be made sythetically.

To overcome the drawbacks of current seroproteomic technologies, we developed a novel functional proteomic approach that utilizes high-throughput immunoprecipitation instead of traditional immunoprecipitation which only utilizes monoclonal antibodies. The Serum Antibodies based SILAC-Immunoprecipitation (SASI) approach utilizes immunoprecipitation by serum antibodies, which is then coupled to quantitative stable isotope labeling by amino acids in cell culture (SILAC) to identify proteins that elicit a changed antibody response. Despite the aggressive nature of pancreatic cancer, seroproteomic approaches have not yet been extensively applied to studying pancreatic ductal adenocarcinomas (PDA) (9, 10). We utilized a vaccine tumor cell line as the proteome to analyze immunized sera from pancreatic cancer patients vaccinated with the GM-CSF vaccine (2). Our study focuses on immunized sera from patients showing a mesothelin-specific post-vaccination T cell response correlated with post-vaccination prolonged disease free survival (2). Using mass spectrometric analysis, the SASI approach comprehensively identified >45 proteins that elicited at least a 2-fold increase in antibody response post-vaccination. We present the first large scale study to identify and categorize proteins that are targeted by antibodies in the human body. The high-throughput SASI approach identifies both proteins that are of low abundance as well as in their native state (conformational epitopes), and provides quantitative measure of the antibody response, including all changes that would not be apparent by traditional western blots.

This approach successfully identified a panel of 13 proteins. Three of these proteins were previously identified by us using the more crude 2-D gel approach followed by mass spectrometry analysis. This older approach identified 17 proteins, but only 2 were found to have biologic importance (Annexin A2 and Galectin-3). As an example, Annexin A2, was found to be differentially expressed by pancreatic cancers (6, 18). In addition, we showed that this protein translocates from the cytosol to the transmembrane through a tyrosine phosphorylation mechanism that confers metastatic potential to pancreatic cancer cells (18). Finally, the antibodies induced by this protein halted metastases. This data provides evidence that antibody targets have biologic importance to cancer (6, 18).

The SASI approach was able to identify proteins that were not found by our prior analysis. Of these proteins, transferrin receptor (TFRC), regulatory subunit 12A of protein phosphatase 1 (PPP1R12A) and regulatory subunit 8 of the 26S proteasome (PSMC5) were shown to be pancreatic cancer associated antigens that are recognized by antibodies in the sera of vaccinated patients who have demonstrated favorable disease free survival. We further analyzed PSMC5, TFRC and PPP1R12A for tissue expression in normal, pre-malignant and pancreatic tumor specimens and found these proteins increase in expression with tumor development. Overall, our data demonstrates that the novel SASI approach can enable identification of candidate proteins as new biomarkers for screening, prediction tools of the vaccine's success, and novel targets for therapeutic intervention.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Materials and Methods

Patients, Serum and Tissue Samples

Patients were enrolled in a phase II study of an allogeneic GM-CSF secreting whole cell pancreatic cancer vaccine in compliance with the Johns Hopkins Medical Institution Institutional Review Board (IRB)-approved J9988 protocol. Blood samples were collected pre-vaccination, 14 days after $1^{st}$ vaccination and 28 days after each subsequent vaccination. Sera was collected by centrifugation, aliquoted and stored at −80° C. Pancreatic tumor tissue samples were obtained from patients prior to vaccination.

Antibody Purification

Antibodies were purified from pre- and post-$3^{rd}$ vaccination sera using a protein G column (GE Healthcare, Piscataway, N.J., USA) as per manufacturer's protocol. Quantification of purified antibodies was done using NanoDrop spectrophotometer (Thermo Fisher Scientific, Waltham, Mass., USA).

Sample Preparation

The human pancreatic cancer cell line, Panc 10.05 was grown as previously described. For the SILAC procedure, Panc 10.05 cells were grown in either light ($^{12}C_6$-Lys, $^{12}C_6$-Arg) or heavy ($^{13}C_6$-Lys, $^{13}C_6$-Arg) RPMI1640 media containing 10% fetal bovine serum and antibiotics in a humidified incubator at 37° C. with 5% CO2. Stable isotope containing amino acids, $^{13}C_6$-arginine and $^{13}C_6$-lysine, were purchased from Cambridge Isotope Laboratories (Andover, Mass., USA). Arginine and lysine-free RPMI1640 media, fetal bovine serum (FBS) and antibiotics (penicillin and streptomycin) were purchased from Invitrogen (Carlsbad, Calif., USA). The light and heavy cells were washed with phosphate buffered saline and were harvested using M-PER buffer (Thermo Fisher Scientific) in the presence of cocktail protease inhibitors (Thermo Fisher Scientific). Protein was quantified using the Lowry method.

Immunoprecipitation for Mass Spectrometry

Equal amounts of light and heavy cell lysates were incubated overnight with purified pre- and post-vaccination antibodies, respectively. On the following day, the two sets of lysate: antibody mixture were each incubated with protein G beads (Invitrogen) and washed using M-PER buffer. The immunoprecipitates were eluted by boiling in NuPAGE® LDS sample buffer (Invitrogen). The light and heavy eluted lysates were mixed 1:1. The mixture was concentrated and resolved by 10% SDS-PAGE. The gel was stained using a coomassie dye staining kit (Invitrogen).

Liquid Chromatography Tandem Mass Spectrometry and Data Analysis

The stained gel was excised into 18 bands and each band was destained in 40 mM ammonium bicarbonate/40% acetonitrile solution. The samples were reduced with 5 mM dithiothreitol/20% acetonitrile solution, alkylated with 100 mM iodoacetamide and digested with trypsin. Sequencing grade modified porcine trypsin was purchased from Promega (Madison, Wis., USA). The peptides were extracted, desalted, dried and reconstituted in 0.1% formic acid. The peptides were analyzed by reversed phase liquid chromatography tandem mass spectrometry (LC-MS/MS). Briefly, the peptides in solution were separated using an on-line reverse phase nano high-performance liquid chromatography using a C18 column and the Eksigent Nano 2D high-performance liquid chromatography (HPLC) pumping system (Eksigent). The nano-HPLC is interfaced directly with the LTQ-Orbitrap-XL (Thermo Electron) allowing for introduction of the separated peptide solution into the mass spectrometer for tandem mass spectrometric analysis. Isolated proteins from each band were identified using an automated database search algorithm, MASCOT, within the Proteome Discoverer software platform (Thermo Electron) and processed by MaxQuant. Our data was searched at a mass tolerance of 10 ppm for MS species and 1 Da for MS/MS with carbamidomethylation of cysteine as a fixed modification and oxidation of methionine as a variable modification. The proteolytic enzyme indicated was trypsin and we allowed up to two missed cleavage events.

Mass-Spectrometry Data Validation

Panc 10.05 cells grown in light RPMI1640 media were lysed in M-PER buffer supplemented with protease inhibitor cocktail. The lysate was immunoprecipitated with either the pre- or post-vaccination purified antibodies using protein G beads. The immunoprecipitates were eluted by boiling in NUPAGE LDS sample buffer and resolved on a NuPAGE 4-12% Bis-Tris gel (Invitrogen). Proteins in the gel were transferred onto nitrocellulose membrane using a semi-dry apparatus (Invitrogen). The membrane was blocked in 5% bovine serum albumin (BSA, Invitrogen) in 0.1% Tween 20-PBS (PBS-T) buffer for 1 hour at room temperature and probed with the relevant primary antibody overnight at 4° C. Antibodies against galectin-3 (sc-19283), E3 ubiquitin protein ligase (sc-9561), mesencephalic astrocyte-derived neurotrophic factor (sc-34560), epidermal growth factor receptor kinase substrate 8-like protein 2 (sc-100722), calpain-1 (sc-81171) were purchased from Santa Cruz Biotechnology (Santa Cruz, Calif., USA). The membrane was incubated with the corresponding peroxidase conjugated secondary antibodies (A8419, Sigma) and then ECL Western Blotting Detection Reagents (GE Healthcare) was used for 1 minute at room temperature for developing.

Western Blot for Detecting Antibody Responses in Patients

Purified recombinant proteins, PSMC5 (TP301251), PPP1R12A (TP323540) and TFRC (TP300980) expressed in human HEK293 cells were purchased from Origene (Rockville, Md., USA). One microgram of purified protein was denatured by boiling in SDS-PAGE sample buffer and resolved on a NuPAGE 4-12% Bis-Tris gel (Invitrogen). Proteins in the gel were transferred onto nitrocellulose membrane using a semi-dry apparatus (Invitrogen). The membrane was cut into individual lanes and was blocked in 5% bovine serum albumin (BSA, Invitrogen) in 0.1% Tween 20-PBS (PBS-T) buffer for 1 hour at room temperature. After blocking, each individual lane was probed with either pre-vaccination or post-vaccination serum of the various patients at 1:1000 dilution. A lane was used as a control and probed with mouse anti-DDK antibody (TA150030, Origene) overnight at 4° C. The membrane was incubated with the peroxidase conjugated secondary antibodies; goat anti-human IgG antibody (A8419, Sigma) for patient serum lanes or rabbit anti-mouse IgG (A9044, Sigma) for control lane. ECL Western Blotting Detection Reagents (GE Healthcare) was used for 1 minute at room temperature for developing.

Immunohistochemistry

Immunohistochemistry was performed on formalin-fixed paraffin-embedded embedded 5 μm thick sections of pancreatic tumor tissue samples for the available 46 of the 60 patients enrolled in the study was obtained from the Department of Pathology at Johns Hopkins Medical Institutions. Standard MC protocol was applied using Bond-Leica autostainer (Leica Microsystems, Bannockburn, Ill.). Briefly, tissue sections were baked for 20 minutes at 65° C. followed by deparaffinization, antigen retrieval and primary antibody incubation at optimal conditions. Bond polymer detection system was applied to develop the reaction. 3',3' diaminobenzidin (DAB) chromogen-substrate was utilized for visualization of reaction as per manufacturer's instructions (Leica Microsystems, Bannockburn, Ill.). All sections were then counterstained with hematoxylin, dehydrated and cover slipped. Antibody information is detailed in the table below.

| Name | Clone/animal species | Dilution | Source |
|---|---|---|---|
| Anti-PSMC5 | Rabbit | 1:150 | HPA017871, Sigma |
| Anti-PPP1R12A | Rabbit | 1:500 | HPA039443, Sigma |
| Mouse anti-Human Transferrin Receptor | Mouse (Clone:H68.4) | 1:2000 | 136800, Invitrogen |

EXAMPLE 2

Design and Validation of Quantitative Proteomic Approach 60 pancreatic cancer patients, who had their pancreas surgically removed, were involved in the study (FIG. 1) (2). The patients received their first vaccination 2 months after surgery. One month after the first vaccination, the patients underwent a 6-month course of chemoradiation. The second, third and fourth vaccines were each administered at sequential one-month intervals from the time of chemotherapy completion. The fifth, and final, vaccination was received 6 months after the fourth vaccination. Serum samples were obtained pre- and post-vaccination for all five vaccinations (2). The 60 vaccinated patients were divided into 3 groups (A, B and C) based on length of disease free survival (DFS) (2). Group A was composed of 12 patients who received all of the scheduled vaccinations and demonstrated a DFS>3 years (prolonged DFS as well as overall survival). The clinical time point cutoff was determined to be 3 years because patients characterized with a 3-year DFS were less likely to have cancer recurrence. The 21 patients in Group B received at least 3 scheduled vaccinations, but had a DFS<3 years. The 27 patients in Group C relapsed before receiving their second scheduled vaccination.

EXAMPLE 3

Identification of Proteins by the SASI Approach

Figure 5A:
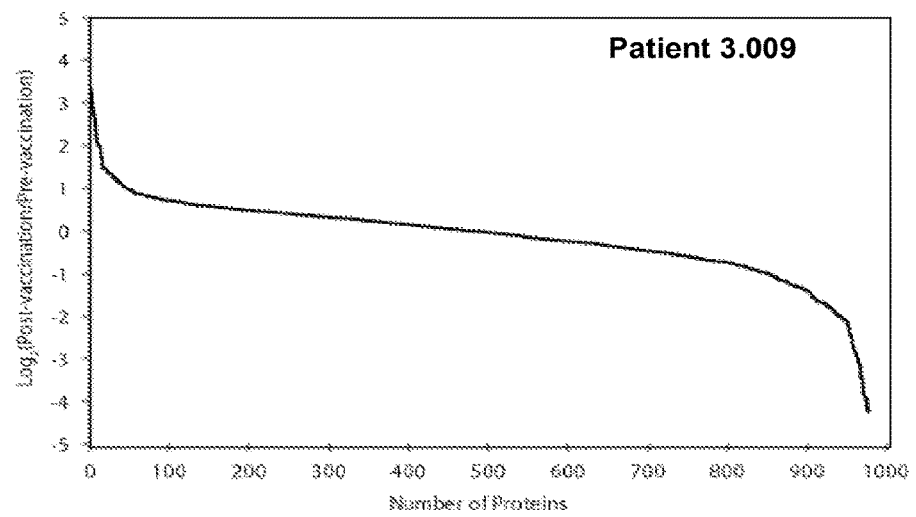
FIG. 5A-5C. Global changes in antibody recognition post-vaccination compared to pre-vaccination of patients 9 (FIG. 5A), 27 (FIG. 5B), and 52 (FIG. 5C), respectively.
Figure 5B:
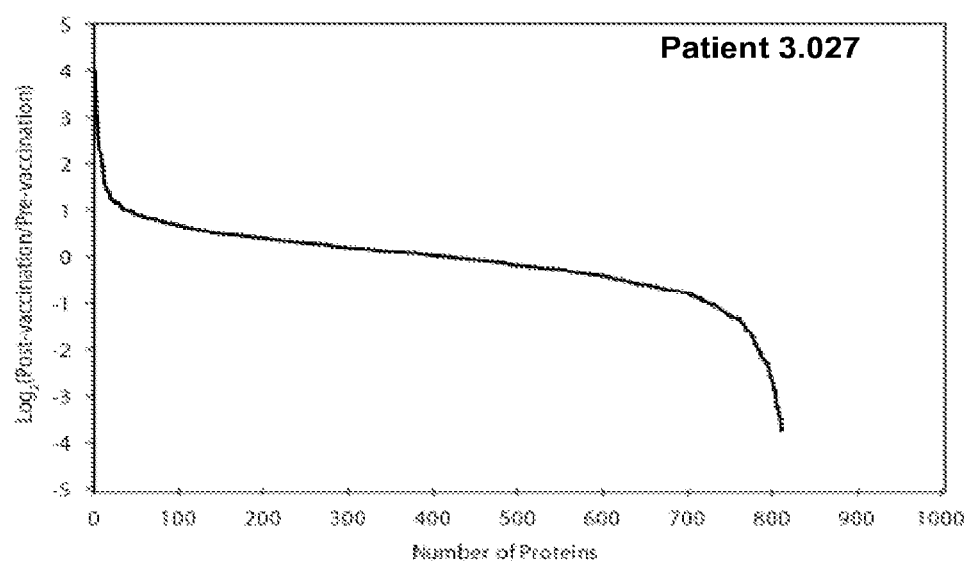
Figure 5C:
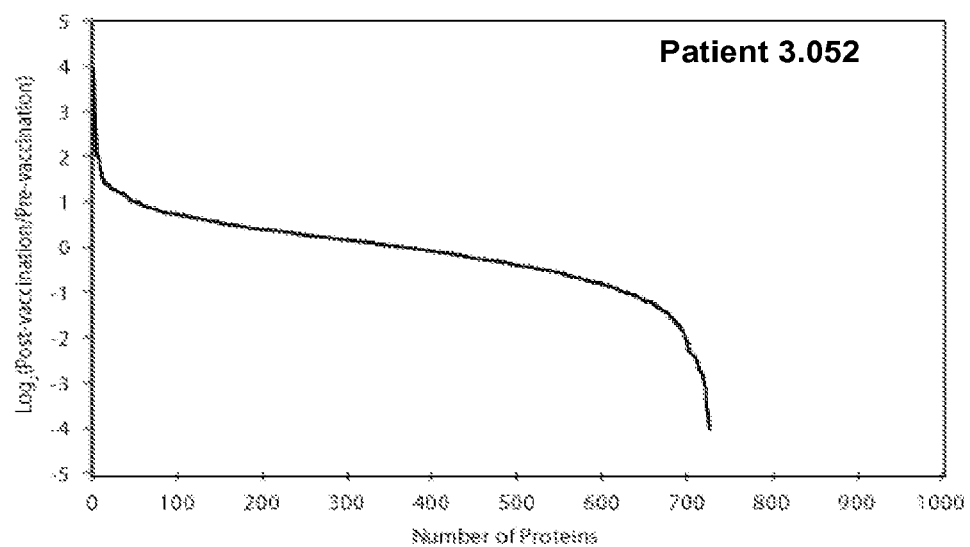

To identify the proteins in the post-vaccination sera of patients in Group A (DFS>3 years), we used the immunized sera from three patients (patients 9, 27 and 52) who demonstrated other evidence of post-vaccination immune responses. We identified a total of 976 proteins for patient 9, 811 proteins for patient 27 and 727 proteins for patient 52 (FIG. 5). A broad range of post-vaccination antibody response was observed; from a 16 fold change increase post-vaccination to a 10 fold change decrease. The majority of the proteins, as expected, had no change in response post-vaccination. We identified 51 proteins for patient 9, 47 proteins for patient 27 and 54 proteins for patient 52 that had a 2 fold change in response. Through the SASI approach, we present the first large scale study to identify and categorize proteins that are targeted by antibodies in the human body.

Pre-vaccination and post-4th vaccination sera from 3 patients, 3.009, 3.027 and 3.052 from Group A was used in the development of the SASI approach.

The SASI approach consists of 4 key components: (a) Antibody purification, (b) SILAC labeling, (c) Immunoprecipitation, and (d) Downstream Analysis.

EXAMPLE 4

(a) Purification of IgGs from Serum

Figure 2:
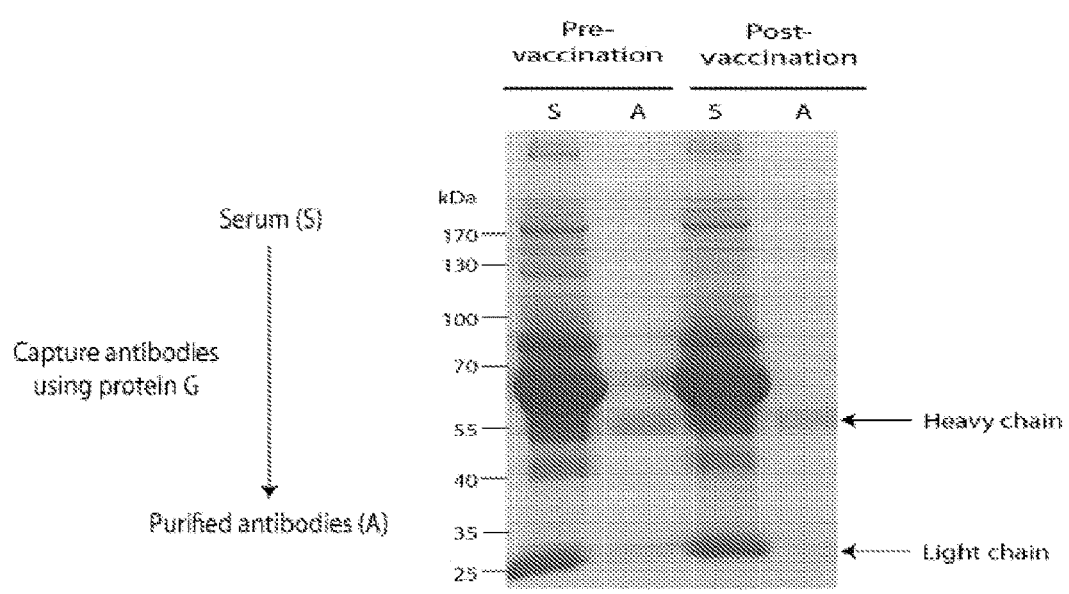
FIG. 2. Purification of human antibodies from serum of vaccinated pancreatic cancer patient. Antibodies (A) were extracted from the pre-vaccination and post-vaccination sera (S) using a protein G column.

Using a Protein G column, we isolated immunoglobulin G (IgG) from the serum (FIG. 2). After washing the column, the IgGs are eluted with a low pH buffer. The eluted IgGs are collected and the pH is neutralized. Thus, functional pancreatic cancer specific IgGs were isolated from the immune sera (FIG. 2).

Table 1 shows a partial list of proteins determined to be biologically relevant in our study. Fold change is defined as the ratio of post-vaccination to pre-vaccination antibody response.

| Protein | Gene symbol | Average fold change | Protein function |
|---|---|---|---|
| Galectin 3 | LGALS3 | 11.0 | Regulator of T-cell functions |
| 26S proteasome, regulatory subunit 8 | PSMC5 | 4.6 | Confers ATP dependency and substrate specificity to the 26S complex |
| MRP-1 | CD9 | 4.1 | Cell adhesion and motility |
| HDGF-2 | HDGFRP2 | 3.2 | Function unknown |
| Centrosomal protein of 170 kDa | CEP170 | 3.1 | Microtubule organization |
| Prohibitin-2 | PHB2 | 2.4 | Mediator of transcriptional repression via recruitment of histone deacetylases |
| Phosphatidylinositol synthase | CDIPT | 2.2 | Phosphatidylinositol biosynthesis |
| Retinol dehydrogenase 11 | RDH11 | 2.0 | Short-chain aldehyde metabolism |
| Aspartate aminotransferase | GOT2 | 1.9 | Amino acid metabolism |
| Protein phosphatase 1, regulatory subunit 12A | PPP1R12A | 1.7 | Regulator of protein phosphatase 1C and mediates binding to myosin |
| Transferrin receptor | TFRC | 1.7 | Iron uptake via endocytosis of transferrin |
| Pyruvate kinase | PKM2 | 1.7 | Glycolytic enzyme generating ATP |
| Annexin A2 | ANXA2 | 1.4 | Cell adhesion |

Of these proteins, galectin-3, annexin A2 and pyruvate kinase were identified previously by a 2-D proteomic approach (17). Galectin-3 and annexin A2 are currently under investigation for their role in pancreatic ductal adenocarcinomas pathogenesis and progression (18). In our studies to discover biologically relevant proteins in pancreatic cancer, we have identified the same proteins through two different proteomic methods. Ongoing research has already shown these proteins are promising targets involved in signaling pathways important to the biology of pancreatic cancer progression and metastasis (17, 18). Therefore, we essentially have ascertained that our approach determines biologically relevant proteins. Overall, the SASI approach comprehensively identified more than 2500 proteins.

EXAMPLE 5

(b) SILAC Labeling

The Panc10.05 cell line was utilized in SILAC labeling experiments. Panc 10.05 is one of the two vaccine tumor cell lines (the proteome), and its use for SILAC labeling would ensure the antibody response is specific to human proteins and would contain the correct post-translational modifications, including glycosylation. Panc 10.05 was grown in both a heavy version form and a light version form. Stable isotope labeling with amino acids in cell culture (SILAC) is a quantitative proteomics method that involves in vivo labeling of proteins followed by mass spectrometric analysis. In this method, Panc 10.05 cells incorporate nonradioactive heavy isotopes of lysines ($^{13}C_6$-Lys) and arginines ($^{13}C_6$-Arg) into its proteome instead of the "light" versions ($^{12}C_6$-Lys and $^{12}C_6$-Arg) present in the commercially available media. Panc 10.05 cells were grown in either "heavy" media containing heavy amino acids or in "light" media containing normal amino acids. After 9 passages, cells grown in heavy and light media were lysed to give heavy and light lysates, respectively.

EXAMPLE 6

(c) Immunoprecipitation

Figure 3:
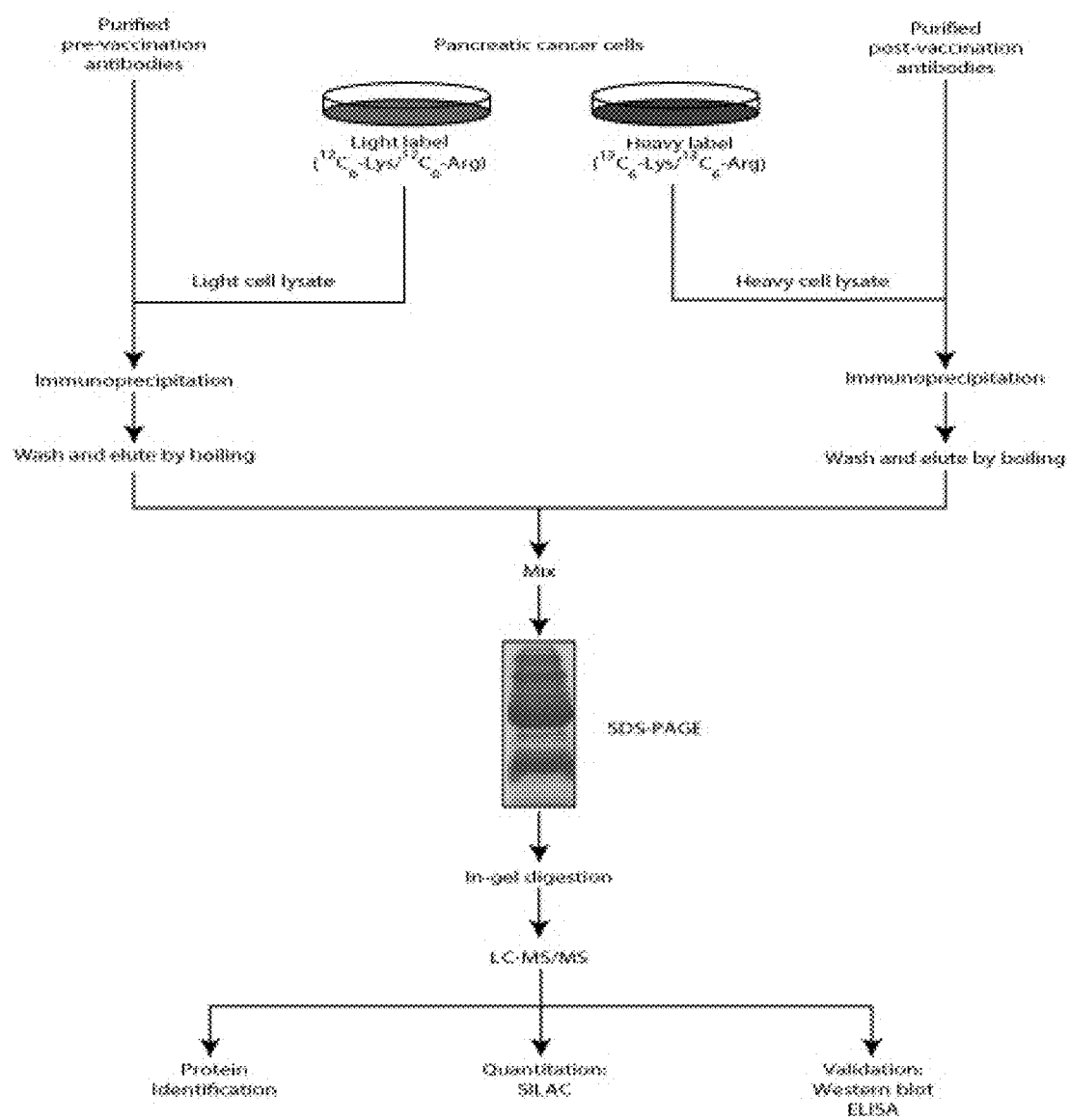
FIG. 3. Outline of the SASI approach.

The light and heavy lysates were subjected to overnight immunoprecipitation, using purified pre- and post-vaccination antibodies, respectively (FIG. 3). The following day, Protein G beads were added to capture the IgGs, which were bound to various proteins from the lysates. Unbound proteins were removed from the beads by a series of washing steps. Boiling the beads in sample buffer allowed elution of the immunoprecipitated proteins and IgGs. This process gave us two sets of samples. One sample consists the eluted heavy proteins with the post-vaccination IgGs, whereas the other sample is the eluted light proteins with the pre-vaccination IgGs. These samples were mixed in a 1:1 ratio. By using equal amounts of heavy and light protein as well as an equal amount of antibodies for immunoprecipitation, we are able to infer that the changes reflected in the heavy to light ratio equates to the changes in the antibody constitution for each antigen. If a protein showed increased antibody response post-vaccination, we would see greater heavy protein to light protein ratio for that protein. If a protein showed decreased antibody response post-vaccination, we would see a lower heavy protein to light protein ratio for the protein.

EXAMPLE 7

(d) Downstream Analysis

The 1:1 heavy and light mixed samples were separated by gel electrophoresis and stained with coomassie dye. 18 protein bands were excised and digested with trypsin. The extracted peptides were analyzed by LTQ-Orbitrap mass spectrometer. The proteins were identified and quantified using Mascot and MaxQuant, respectively.

We wanted to further validate the SILAC data derived from mass-spectrometry analysis. We used pre-vaccination and post-vaccination antibodies of patient 3.052 for immunoprecipitation with light cell lysates in both cases (FIG. 4). Our SILAC data using patient 52 had revealed that galectin-3, E3 ubiquitin-protein ligase UBR5 and mesencephalic astrocyte-derived neurotrophic factor had an increased antibody response post-vaccination by 15.3, 4.0 and 3.9 fold respectively. Contrastingly, this patient also showed a decreased antibody response post-vaccination for calpain-1 and epidermal growth factor receptor kinase substrate 8-like protein 2 by 2.5 and 10.0 fold respectively. To validate our SILAC data, we conducted Western blots for these proteins. The immunoprecipitated proteins were separated by SDS- PAGE followed by western blot using antibodies against the following proteins: galectin-3, E3 ubiquitin-protein ligase UBR5, mesencephalic astrocyte-derived neurotrophic factor, calpain-1 and epidermal growth factor receptor kinase substrate 8-like protein 2. We saw that there was a dramatic increase in galectin-3 protein level in the post-vaccination blot, whereas E3 ubiquitin-protein ligase UBR5 and mesencephalic astrocyte-derived neurotrophic factor showed a modest increase in detection post-vaccination. Similarly, calpain-1 showed a dramatic decrease in detection whereas epidermal growth factor receptor kinase substrate 8-like protein 2 showed a modest decrease in the blot containing the post-vaccination immunoprecipitated proteins. The western blot analysis, though not quantitative, mirrored the trends we observed from our quantitative mass-spectrometry derived SILAC ratios.

EXAMPLE 8

PSMC5, PPP1R12A and TFRC are Antibody Targets of Immune Response Against PDA

Our interest focused on proteins that had greater than 1.5 fold change response. Previous proteomic approaches had identified annexin A2 as biologically relevant. In the SASI approach, annexin A2 revealed a 1.4 fold change in response post vaccination. From there, we set an average 1.5 fold change post-vaccination with at least one of the 3 sera tested showing a 2 fold change as our benchmark for a biologically relevant response. However, some of these proteins had an increased post-vaccination response in 2 or all of the sera tested by the SASI approach. We further decided to test if there was a correlation between the increased post-vaccination antibody response and disease free status.

Using purified recombinant proteins, we examined the post-vaccination response in patients with favorable DFS. For this experiment, we used the serum before the first vaccination as the pre-vaccination serum, while the serum after the $3^{rd}$ vaccination was designated the post-vaccination serum. PSMC5, PPP1R12A and TFRC showed elevated antibody titers in patients with favorable DFS (FIG. 6). PSMC5 elicited an increased antibody response in 8 of 12 patients. TFRC elicited an increased antibody response in 8 of 12 patients. PPP1R12A elicited an increased antibody response in 9 of 12 patients. Interestingly, these 3 proteins also demonstrated an increased antibody response in each of the 3 patients who were tested in the SASI approach. Although, we cannot correlate the quantitiative SASI approach data with the qualitative Western blot results, the overall trends were similar. This observation further provided validation of our SASI results.

We then wanted to compare the patients with DFS>3 years to those with DFS<3 years (FIG. 6). For this comparison, we selected 12 out of the 21 patients in the group with DFS<3 years. The selection was based on the level of vaccinations completed. Each of these 12 patients had received at least 3 vaccinations, allowing us to compare the post-vaccination serum to the pre-vaccination serum. Western blot analysis showed an increase in antibody response post-vaccination to recombinant both PSMC5 and TFRC in only 2 of the 12 patients that showed DFS<3 years (compared to 8 of the 12 patients with DFS>3 years). Western blot analysis showed an increase in antibody response post-vaccination to recombinant PPP1R12A in 5 of the 12 patients that showed DFS<3 years (compared to 9 of the 12 patients with DFS>3 years). Interestingly, 4 of the 12 patients with DFS<3 years showed a decreased antibody response to PPP1R12A post-vaccination, whereas only 1 of the 12 patients with DFS>3 years showed a decreased response post-vaccination. Similarly, both PSMC5 and TFRC demonstrated a decreased antibody response in 2 out of the 12 patients DFS<3 years (compared to only 1 patient with DFS>3 years showing a decreased response). These results imply that the vaccine-induced antibody response to PSMC5, PPP1R12A and TFRC have strong correlations to clinical benefit. A decreased response post-vaccination for these proteins is comparable to a shorter DFS. Data suggests that these proteins are antigenic targets of vaccine-induced humoral responses in pancreatic cancer patients. Most significantly, the antibody responses detected against these proteins in patients with >3 years disease-free survival suggests an anti-tumor potential of targeting these proteins.

EXAMPLE 9

Increased PSMC5, PPP1R12A, TFRC Tissue Expression Correlates with PDA Development Next, we wanted to examine the cause behind the antibody response. There are 3 main reasons for how these self proteins could induce an altered antibody response in the patients: difference in expression levels, difference in localization, or post-translational modifications. The reports on levels of PSMC5 and PPP1R12A in pancreatic cancer or other cancers are very preliminary with no extensive information.

Figure 7A:
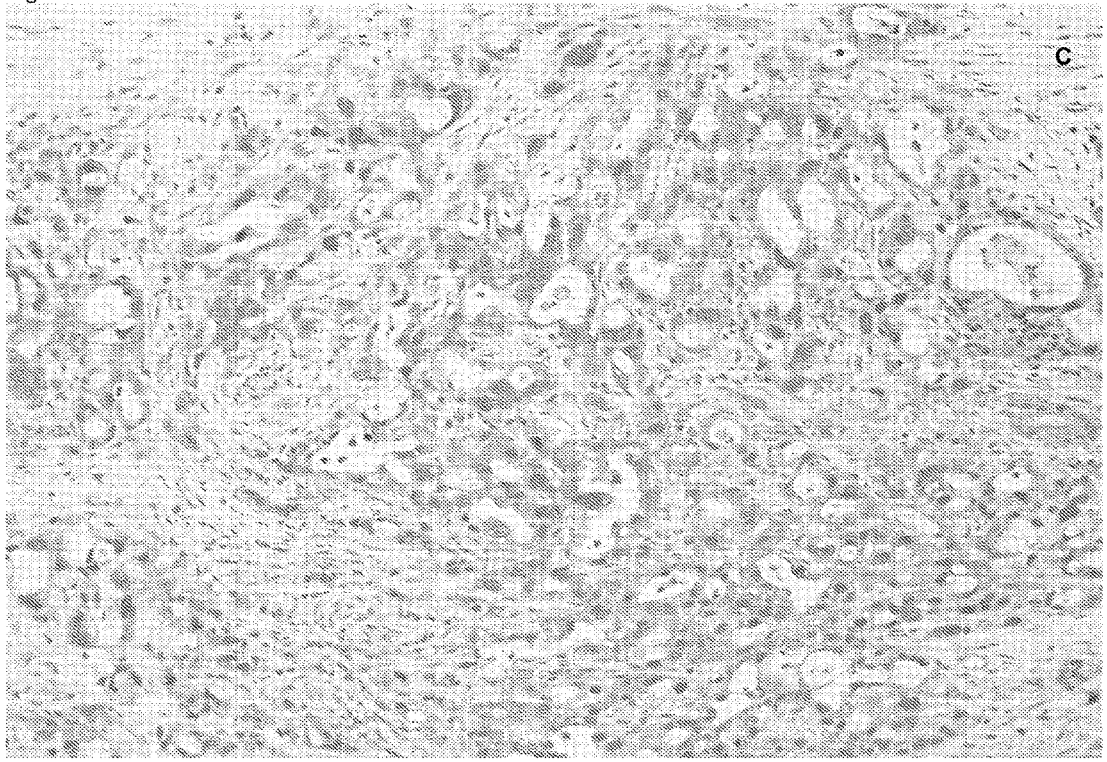
Figure 7B:
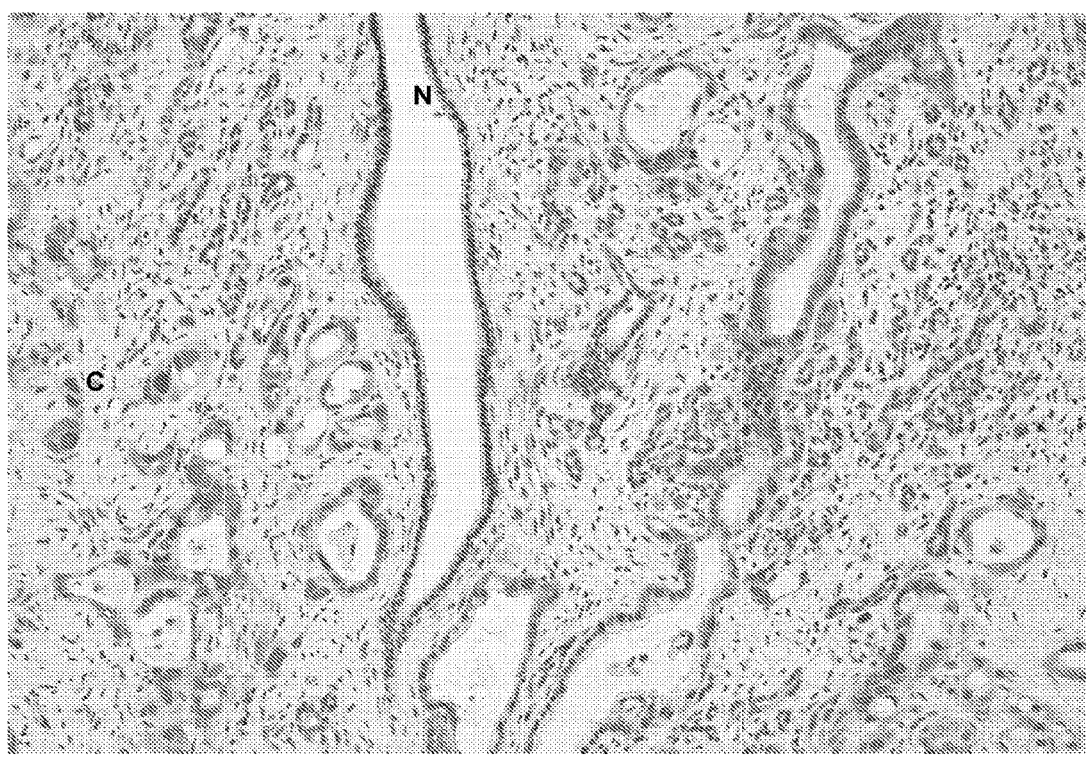

First, we analyzed the expression levels and localization of PSMC5 (FIG. 7) in normal as well as cancer tissues by immunohistochemistry (IHC). The resected tumors for this study came from 46 of the 60 patients who were treated in our Phase II study and were available for staining. With immunohistochemistry, we found that normal pancreatic epithelial ductal cells display weak cytoplasmic staining for PSMC5. However, ductal carcinoma cells display strong cytoplasmic staining. PSMC5 is overexpressed in pancreatic cancer compared to normal tissue. Specifically, 85% of pancreatic tumor cells have increased expression of PSMC5. PSMC5 is a part of the 26S proteasome, which is present in all cells; however, normal cell level of PSMC5 is very low. Normal duct tissue stained very weakly for PSMC5 (only 15%) in the cytoplasm, with almost no nuclear staining observed. Additionally, we observed that PSMC5 localizes to the nucleus in cancer cells, which is shown by the intense staining in the nucleus of cancer cells. The cytoplasmic and nuclear expression increases with the progression from pancreatic intraepithelial neoplasia (PanINs) to PDA. Our data shows that 50% of the pancreatic tumor cells have increased nuclear staining of PSMC5. Contrastingly, only 5% of normal duct cells, acinar cells, blood vessels show nuclear staining of PSMC5. The isotype controls demonstrated complete negative staining in the 10 slides examined. This data provides evidence that PSMC5 is overexpressed in PDA and furthermore, the nuclear expression of PSCM5 increases from normal to cancer tissue. The cancer-specific increase in PSMC5 provides support to the idea that the protein is a potential immunologic target.

EXAMPLE 10

Abnormal Subcellular Localization

Figure 8A:
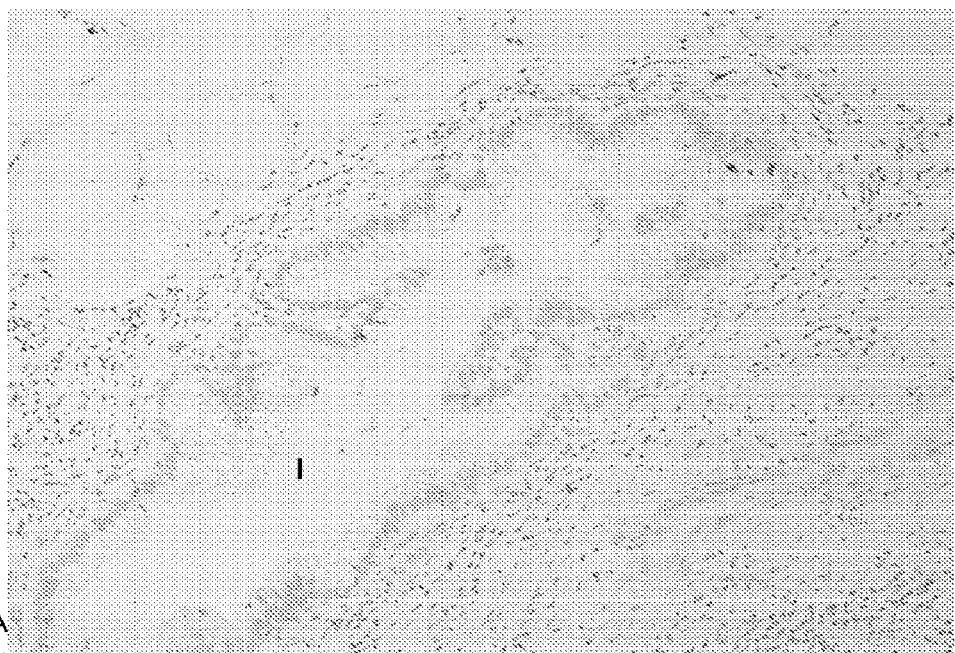
Figure 8B:
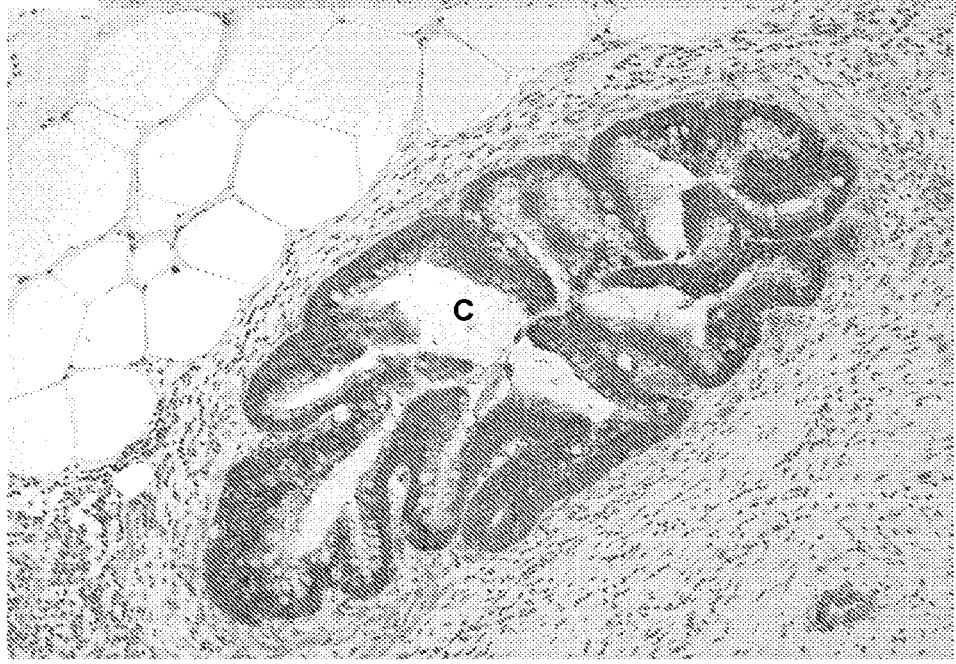
Figure 8C:
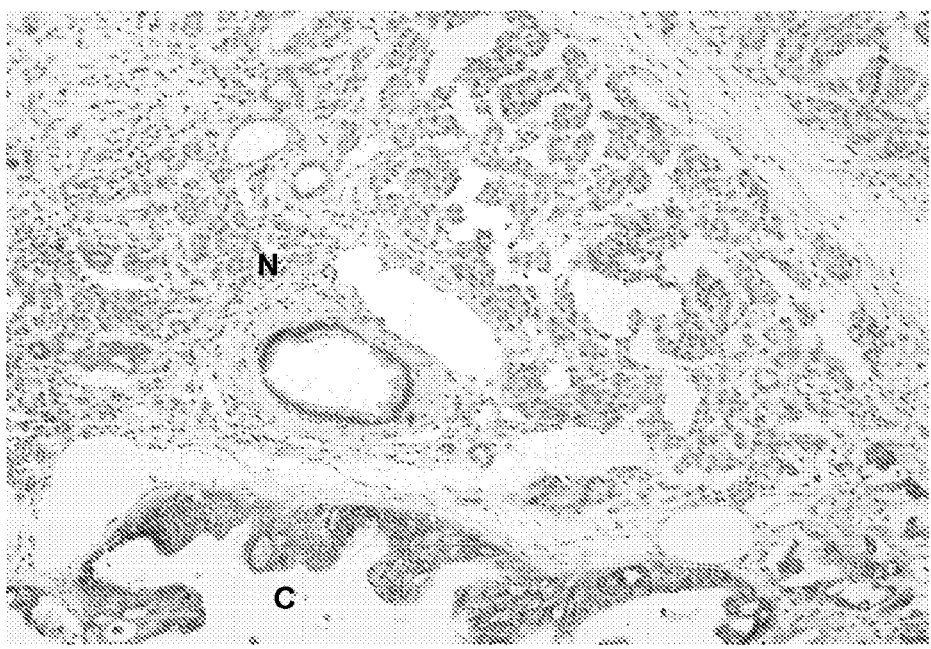
Figure 9:
Figure 11:
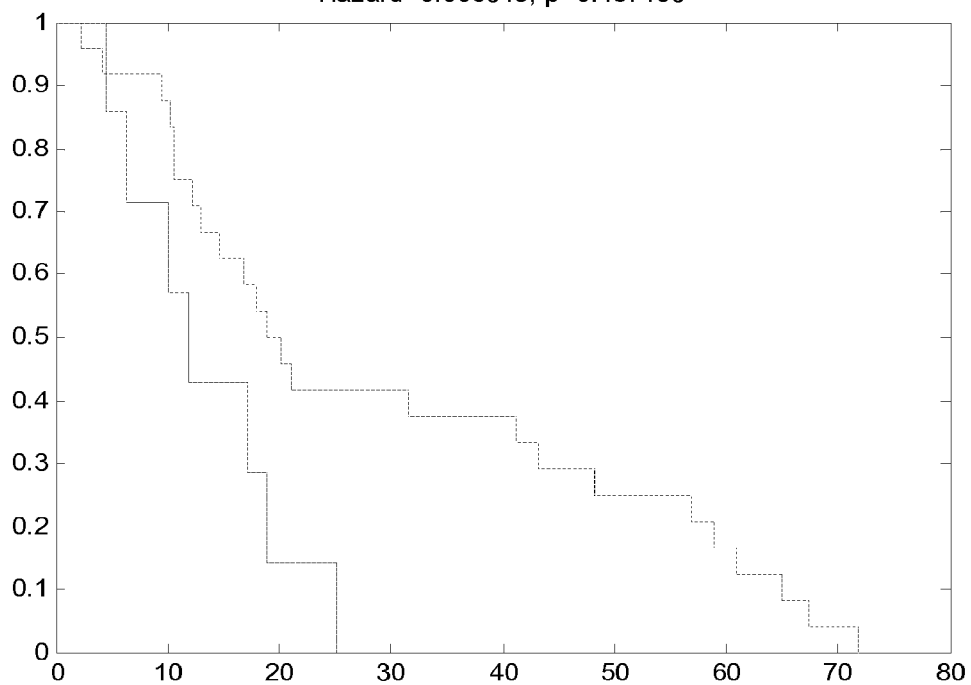
FIG. 11. Correlation between patient tissue expression of marker post-surgery and survival post-treatment with vaccine. Higher PSMC5 expression correlates with improved survival post-vaccination FIG. 12. Correlation between patient tissue expression of marker post-surgery and survival post-treatment with vaccine. Higher PPP1R12A expression correlates with improved survival post-vaccination.
Figure 12:
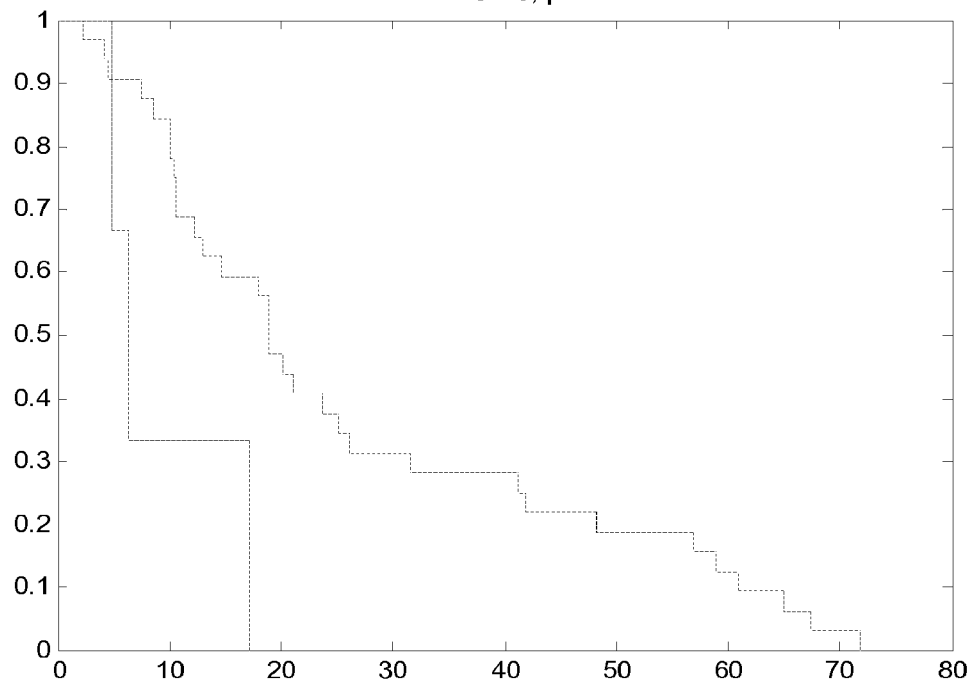

PPP1R12A or MYPT1 is part of the Rho Kinase pathway component. We analyzed the expression levels as well as localization of PPP1R12A (FIG. 8) in normal and cancer tissues by immunohistochemistry (MC). Through immunohistochemistry, we found that normal pancreatic epithelial ductal cells display weak cytoplasmic staining. Contrastingly, the ductal carcinoma cells displayed strong cytoplasmic staining. PPP1R12A was found to be overexpressed in pancreatic cancer compared to normal tissue. Specifically, 82% of the cancer cells have increased expression of PPP1R12A. Only 2% of normal duct cells stained very weakly for PPP1R12A, with no membrane staining seen in these cells. We also observed PPP1R12A to be localized to the membrane and stained strongly and intensely in the cancer cells. The membrane localization was only observed in PDA cells. We showed that about 20% of PDA cells have increased membrane staining of PPP1R12A. On the contrary, the normal duct cells, acinar cells, blood vessels showed no membrane staining of PPP1R12A. This data provides support that PPP1R12A is overexpressed in PDA and that membrane expression of PPP1R12A is a unique feature of cancer. Thus, PPP1R12A is a potential immunologic target. TFRC staining were similar to those of PPP1R12A. 74% of PDA cells stained strongly for TFRC whereas only 1% of the normal duct cells showed very weak staining (FIG. 9). We also observed some membrane TFRC staining in only the PDA cells. Similar to PSMC5, both PPP1R12A and TFRC showed increased staining as the normal duct cells progressed to the PanIN stages to the full blown PDA disease.

Thus, the SASI approach has been able to successfully identify biologically relevant proteins, all 3 of which could be extensively validated. We saw that each of the 3 markers, PSMC5, PPP1R12A and TFRC, increases in expression when we compare normal to cancer cells. Furthermore, there is evidence of mislocalization of these proteins in cancer. In cancer, PSMC5 is found abnormally in the nucleus, and PPP1R12A and TFRC are also found on the cell membrane. Both overexpression and mislocalization in the cancer cells help explain why an antibody response was targeted towards these proteins. PSMC5, PPP1R12A, and TFRC have great potential, both as immunologic targets as well as diagnostic biomarkers. The heterogeneous nature of both the cancer as well as the antibody responses illustrates a need for a biomarker panel in order not only to cover more patients but also retain high specificity.

EXAMPLE 11

Proteins Eliciting Antibody Responses in Vaccinated Pancreatic Cancer Patients are Expressed by a Range of Adenocarcinomas Background: Developing targets that identify patients for appropriate therapies is a key goal of cancer research. A high throughput proteomic screen identified two proteins, PPP1R12A and PSMC5, which were found to enhance antibody responses in pancreatic cancer patients participating in a phase II trial of an allogeneic, GMCSF-secreting vaccine. Responses to these proteins correlated with increased disease free survival in trial patients. We sought to define PPP1R12A and PSMC5 expression in pancreatic and other common solid malignancies.

Design: Tissue microarrays (TMA) of pancreatic, breast, biliary, lung, liver, and colon carcinomas were stained for PPP1R12A and PSCM5. The intensity of tumor cell expression was scored for each protein from no specific (0); greater than background (1) or strong (2) staining. The percentage of tumor cells expressing each protein and the cellular compartment (cytoplasmic, membranous) was recorded. Positive staining=a score of 1-2 in >25% of cells.

Results: Expression of PPP1R12A was seen in pancreatic (97%), biliary (58%), colon (46%) ER+ breast (37%) and HER-2+ breast (17%) adenocarcinomas. Minimal expression was seen in lung (8%) and basal breast (4%) adenocarcinomas. A higher percentage of pancreatic cancer expressed PPP1R12A compared to other tumors (p<0.0001). Significantly more ER+ breast carcinomas expressed PPP1R12A than HER-2+ or basal type (p<0.001). Membranous PPP1R12A staining was observed only in pancreas (45%) and colon (30%) cancers. PSMC5 expression was present in all tumors types: pancreatic (57%), ER+ breast (97%), HER-2+ breast (82%), basal breast (86%), liver (69%), biliary (24%), colon (58%), and lung (74%). Breast tumors showed particularly high expression of PSMC5. Additionally, HER-2+ tumors consistently showed expression by 100% of cells within an individual TMA, which was significantly more than either ER+ or basal type breast tumors (p<0.01).

Conclusions: Our study confirms strong expression of both PPP1R12A and PMSC5 in pancreatic cancer. In addition, we identify a range of adenocarcinomas with expression of PPP1R12A and/or PMSC5 including breast, biliary, lung, colon, and liver. This identifies tumor types that might respond to GVAX immunotherapy and provides rationale to direct therapy based on these proteins expression patterns. Membranous expression of PPP121RA in pancreatic and colon cancers is particularly attractive for therapeutic targeting. Additional studies are needed to evaluate the relationship between tumor evolution in these adenocarcinomas and the expression of PPP1R12A and PMSC5.

The invention claimed is:

1. A method of treating a human with a tumor selected from the group consisting of pancreas, breast, biliary, lung, colon, and liver, comprising: administering a pancreatic cancer vaccine composition to the human whereby an immune response to regulatory subunit 12A of protein phosphatase 1 (PPP1R12A) and/or regulatory subunit 8 of the 26S proteasome (PSMC5) is raised and measured in the human.

2. The method of claim 1 wherein prior to said step of administering a sample of the tumor is tested and expression of PPP1R12A and/or PSMC5 on cell membranes of the tumor is detected.

3. The method of claim 1 wherein the vaccine is GM-CSF vaccine (GVAX).

* * * * *